(12) United States Patent
Sakamoto

(10) Patent No.: US 7,410,617 B2
(45) Date of Patent: Aug. 12, 2008

(54) SAMPLE HANDLING PLATE

(75) Inventor: Yasuyuki Sakamoto, Tokyo (JP)

(73) Assignee: Enplas Corporation, Kawaguchi-shi (JP)

( * ) Notice: Subject to any disclaimer, the term of this patent is extended or adjusted under 35 U.S.C. 154(b) by 104 days.

(21) Appl. No.: 11/009,349

(22) Filed: Dec. 10, 2004

(65) Prior Publication Data

US 2005/0106074 A1   May 19, 2005

(51) Int. Cl.
     B01L 3/00   (2006.01)
(52) U.S. Cl. ..................... 422/102; 422/104
(58) Field of Classification Search ............ 422/102, 422/104
     See application file for complete search history.

(56) References Cited

U.S. PATENT DOCUMENTS

| | | | | |
|---|---|---|---|---|
| 4,777,021 A | * | 10/1988 | Wertz et al. | 422/101 |
| 5,456,360 A | * | 10/1995 | Griffin | 206/443 |
| 5,888,834 A | * | 3/1999 | Ishikawa et al. | 436/518 |
| 6,027,695 A | | 2/2000 | Oldenburg et al. | |
| 6,045,760 A | * | 4/2000 | Aizawa et al. | 422/104 |
| 6,258,326 B1 | * | 7/2001 | Modlin | 422/102 |
| 6,426,050 B1 | * | 7/2002 | Pham et al. | 422/104 |
| 6,908,760 B2 | * | 6/2005 | Cima et al. | 435/288.4 |
| 6,982,431 B2 | * | 1/2006 | Modlin et al. | 250/573 |

FOREIGN PATENT DOCUMENTS

| | | |
|---|---|---|
| JP | 7-115958 | 5/1995 |
| JP | 2000-310613 | 11/2000 |
| JP | 2001-17155 | 1/2001 |
| JP | 2003-4742 | 1/2003 |
| JP | 2003-130879 | 5/2003 |

* cited by examiner

*Primary Examiner*—Jill Warden
*Assistant Examiner*—Natalia Levkovich
(74) *Attorney, Agent, or Firm*—Bachman & LaPointe, P.C.

(57) ABSTRACT

A sample handling plate 1 has wells 4 on the side of the surface 1a thereof, and lightening portions 6 on the side of the reverse 1b thereof, each of the wells 4 substantially having the same shape and volume as those of each of the lightening portions 6 so that the amount of shrinkage on the side of the surface 1a is equal to that on the side of the reverse 1b during cooling after the injection molding.

18 Claims, 13 Drawing Sheets

Longitudinal Direction

Lateral Direction

Longitudinal Direction

Lateral Direction

SAMPLE HANDLING PLATE

BACKGROUND OF THE INVENTION

1. Field of the Invention

The present invention relates generally to a sample handling plate used for analyzing very small amounts of various samples (e.g., micro vital substances such as viruses and bacteria, vital formations such as cells and biopolymers, organic compounds other than biopolymers, inorganic substances and inorganic compounds). More specifically, the invention relates to a sample handling plate of a plastic, glass or the like, which is capable of being used for simultaneously examining the functions of a large number of genes and which is also capable of being used as a reactor in the PCR method for amplifying DNAs.

2. Description of the Prior Art

In recent years, of various methods for examining the functions of genes, the micro array technique capable of simultaneously examining thousands kinds to tens of thousands kinds of genes has been particularly noticed in the field of genome medical science and biochemistry.

In such a technical background, as shown in FIG. 24, there has been proposed an apparatus for holding small volumes of liquids, wherein a large number of substantially pyramidal minute wells (recessed portions) 101 are formed in a single flat plate 100 and wherein various liquid samples to be analyzed can be injected into the wells 101 to be simultaneously analyzed (see, e.g., U.S. Pat. No. 6,027,695).

As shown in FIG. 25, there has been also proposed a technique for forming a large number of protrusions 103 on the surface of a plate 102 to hold culture tissues or samples to be analyzed on the top faces 104 of the protrusions 103 (see Japanese Patent Laid-Open Nos. 7-115958 and 2003-4742).

As shown in FIG. 26, there has been also proposed an electrophoresis chip wherein fine grooves (recessed portions) 105 for moving a sample due to electrophoresis are formed in the surface 107 of a plate 106 for separating and extracting a chargeable substance (see, e.g., Japanese Patent Laid-Open No. 2000-310613).

In addition, there has been proposed a technique wherein a large number of samples are allowed to adhere to the surface of a flat plate at dense scattered points (see, e.g., Japanese Patent Laid-Open No. 2003-130879).

Moreover, as shown in FIG. 27, there has been proposed a plastic plate 108 which is capable of being used for carrying out tissue culture and immune analysis and which is capable of being used for many purposes, such as observation of morphology, measurement of absorbance, and measurement of fluorescence and fermentation. This plastic plate 108 is a plate of a transparent resin having a thickness of 0.5 mm or less and having a large number of wells 110 for housing therein a sample, and the plastic plate 108 is held in a holder 111 having a thickness of 1.0 mm or more (see Japanese Patent Laid-Open No. 2001-17155).

However, in the plates 100 and 102 disclosed in U.S. Pat. No. 6,027,695 and Japanese Patent Laid-Open Nos. 7-115958 and 2003-4742, the shape of the surface having the large number of wells (recessed portions) 101 or protrusions 103 is quite different from the shape of the reverse having no wells 101 or protrusions 103. Therefore, if the plate 100 or 102 is formed by the injection molding, the shrinkage percentage on the side of the surface is different from that on the side of the reverse during the injection molding, so that there are some cases where the resin plate 100 or 102 may warp as shown in FIG. 28.

If the plate 106 disclosed in Japanese Patent Laid-Open Nos. 2000-310613 and 2003-130879 is formed of a resin material, there are some cases where the plate 106 may warp due to the temperature difference between the surface and reverse sides since there are some cases where the plate 106 may be heated for promoting hybridization or the like (see FIG. 28).

When the plate 100, 102 or 106 thus warps, if a sample is measured by an optical measuring unit having a narrow focal point using laser beams or the like, the position of the focal point is displaced, so that there is the possibility that the precision of measurement deteriorates. Furthermore, as measures to prevent the warpage of the plates 100 and 102 disclosed in U.S. Pat. No. 6,027,695 and Japanese Patent Laid-Open Nos. 7-115958 and 2003-4742, it is effective to form a plate having a constant thickness as the plastic plate 108 disclosed in Japanese Patent Laid-Open No. 2001-17155. However, the technique disclosed in Japanese Patent Laid-Open No. 2001-17155 is directed to the plastic plate 108 wherein the volume of each well 110 is about one hundred microliters, so that the technique can not be used for forming such a small plate that the volume of each well 110 is about tens nanoliters. That is, if wells 110 having a very small volume of about tens nanoliters are densely formed, it is difficult to form the plastic plate 108 by the injection molding so that the plate 108 has a constant thickness.

Furthermore, if a plate of a material, such as a glass, other than plastics is used as a sample handling plate, the same warpage of the plate as that of a plastic plate may be caused. Therefore, it is desired to take measures to prevent such warpage.

SUMMARY OF THE INVENTION

It is therefore an object of the present invention to eliminate the aforementioned problems and to provide a sample handling plate capable of being prevented from warping when being produced and capable of being used for carrying out a precise measurement by means of an optical measuring unit having a narrow focal point.

In order to accomplish the aforementioned and other objects, according to one aspect of the present invention, a sample handling plate comprises: a plate body having a surface and a reverse; a plurality of fine recessed portions formed in the surface of the plate body; and a recessed portion serving as a lightening portion formed in the reverse of the plate body, the lightening portion being formed so as to have a volume which is substantially equal to a total volume of all of the recessed portions.

According to another aspect of the present invention, a sample handling plate comprises: a plate body having a surface and a reverse; a plurality of first fine recessed portions formed in the surface of the plate body; and a plurality of second fine recessed portions serving as lightening portions formed in the reverse of the plate body, the lightening portions being formed so as to have a total volume which is substantially equal to a total volume of all of the first fine recessed portions. In this sample handling plate, each of the plurality of lightening portions may have the same shape as that of each of the plurality of first fine recessed portions. In this case, the plurality of first fine recessed portions may be arranged at intervals, and the plurality of lightening portions may be arranged at the same intervals as those of the plurality of first fine recessed portions so as to be displaced from the plurality of first fine recessed portion by half of each of the intervals. Alternatively, the plurality of lightening portions and the plurality of first fine recessed portions may be arranged so as to be symmetrical with respect to a central plane in thickness directions of the plate body.

According to another aspect of the present invention, a sample handling plate comprises: a plate body having a surface and a reverse; a frame portion connected to the plate body so as to surround an outer periphery of the plate body; a plurality of first fine protrusions formed on the surface of the plate body; a plurality of second fine protrusions formed on the reverse of the plate body, each of the plurality of second fine protrusions having the same shape as that of each of the plurality of first fine protrusions, wherein the plurality of first fine protrusions and the plurality of second fine protrusions are arranged so as to be symmetrical with respect to a central plane in thickness directions of the plate body.

According to another aspect of the present invention, a sample handling plate comprises: a plate body having a surface and a reverse; a fine recessed portion formed in the surface of the plate body; and a reinforcing rib formed on the reverse of the plate body so as to protrude.

According to another aspect of the present invention, a sample handling plate comprises: a plate body of a resin material having a surface and a reverse; a fine recessed portion formed in the surface of the plate body; and a member formed on the side of the reverse of the plate body so as to be integrated therewith, the member being made of a material having a lower coefficient of thermal expansion than that of the resin material.

According to a further aspect of the present invention, a sample handling plate comprises: a substantially flat plate body having a surface for allowing very small amounts of samples to adhere thereto at scattered points, and a reverse; and a reinforcing rib formed on the reverse of the plate body.

According to a still further aspect of the present invention, a sample handling plate comprises: a substantially flat plate body of a resin material having a surface for allowing very small amounts of samples to adhere thereto at scattered points, and a reverse; and a member formed on the side of the reverse of the plate body so as to be integrated therewith, the member being made of a material having a lower coefficient of thermal expansion than that of the resin material.

According to the present invention, when a plurality of recessed portions are formed in the surface of a sample handling plate, a plurality of recessed portions serving as lightening portions are formed in the reverse of the sample handling plate so that the amount of shrinkage on the side of the surface of the sample handling plate is substantially equal to that on the side of the reverse thereof, and when a plurality of protrusions are formed on the surface of a sample handling plate, a plurality of protrusions are formed on the reverse of the sample handling plate so as to correspond to the protrusions on the surface thereof so that the amount of shrinkage on the side of the surface is substantially equal to that on the side of the reverse.

In an embodiment of the present invention, the warpage of a sample handling plate is suppressed by a reinforcing rib formed on the side of the reverse of the plate, or by a member, such as a metal body, which is formed on the side of the reverse of the plate so as to be integrated therewith, the member being made of a material having a lower coefficient of shrinkage than that of plastics.

According to the present invention, the same measures as those taken for a sample handling plate of a plastic may be taken for a plate of a material, such as a glass, other than plastics to suppress the warpage of the plate.

According to the present invention, the amount of shrinkage on the side of the surface of the sample handling plate can be substantially equal to that on the side of the reverse thereof after the injection molding, so that it is possible to suppress the warpage of the sample handling plate. It is also possible to suppress the warpage of the sample handling plate by the reinforcing rib formed on the side of the reverse of the sample handling plate, or by the metal body formed on the side of the reverse of the sample handling plate so as to be integrated therewith. Thus, measuring light emitted from an optical measuring unit can be easily focused on a sample held on or housed in the sample handling plate.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of a sample handling plate according to the present invention will be described below in detail.

Figure 1:
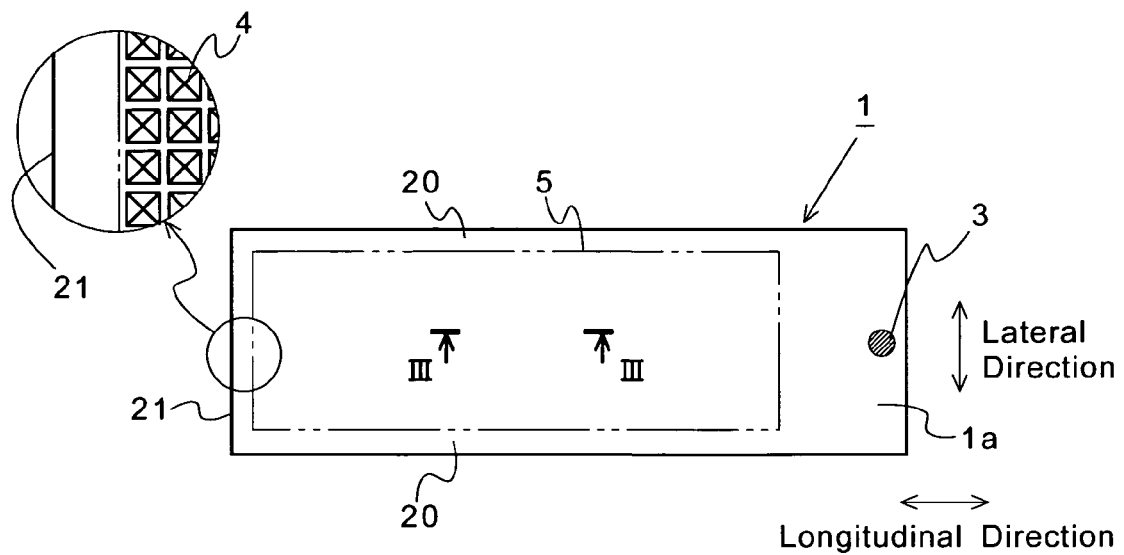
FIG. 1 is a plan view of a preferred embodiment of a sample handling plate according to the present invention.
Figure 2:
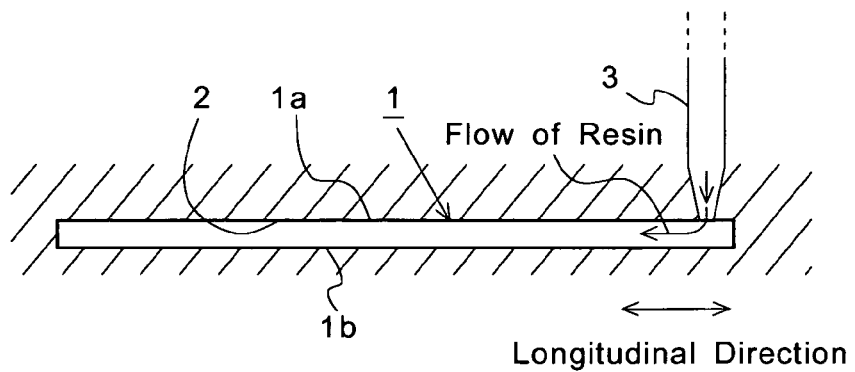
FIG. 2 is a side view of a part of the sample handling plate of FIG. 1, which shows the relationship between a cavity and an injection molding gate and the sample handling plate serving as a product.
Figure 3:
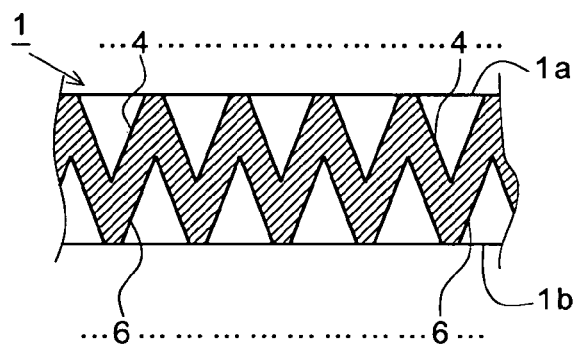
FIG. 3 is an enlarged sectional view taken along line III-III of FIG. 1.

FIGS. 1 through 3 show a preferred embodiment of a sample handling plate 1 according to the present invention. FIG. 1 is a plan view of the sample handling plate 1. FIG. 2 is a side view of the sample handling plate 1, which shows the relationship between a cavity 2 and an injection molding gate 3 and the sample handling plate 1 during the injection molding. FIG. 3 is an enlarged sectional view of the sample handling plate 1 taken along line III-III of FIG. 1.

As shown in these figures, the sample handling plate 1 is a plate-shaped member having a rectangular planar shape which substantially has the same size as that of a slide glass and which has a thickness of about 1.0 mm to about 1.5 mm. The sample handling plate 1 is made of, e.g., polycarbonate (PC), polymethyl methacrylate (PMMA) or an ultraviolet curable resin. The surface 1a of the sample handling plate 1 has a large number of wells (recessed portions) 4 for housing therein a solution (sample) containing DNA fragments or specimens (e.g., cDNAs treated with a fluorescence dye) Each of the wells 4 is a recessed portion having a circular or square opening, the diameter or length of a side of which is in the range of from about 0.2 mm to about 1.0 mm, preferably from 0.2 mm to 0.5 mm. Such thousands wells 4 are arranged at intervals of about 0.3 mm to about 1.0 mm, preferably 0.3 mm to 0.5 mm, in a well forming region 5 of the surface 1a of the sample handling plate 1 so that each of the wells 4 can house therein a sample having a volume of tens nanoliters.

Figure 4A:
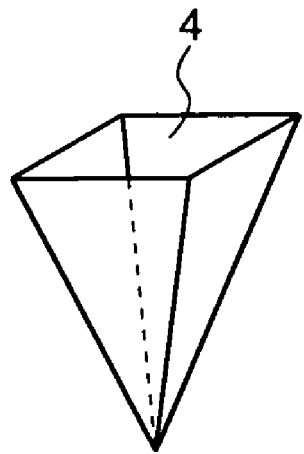
FIGS. 4A through 4D are perspective views showing the shape of a well.
Figure 4B:
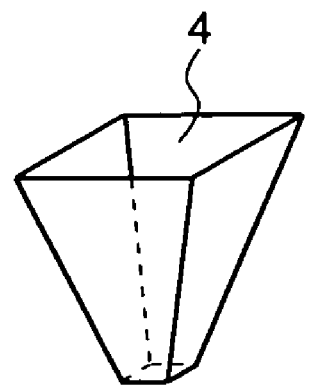
Figure 4C:
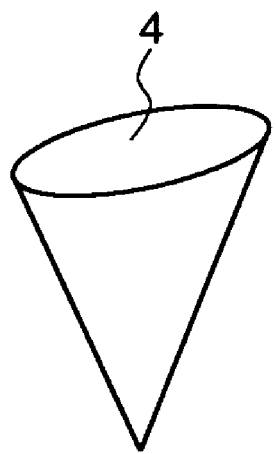
Figure 4D:
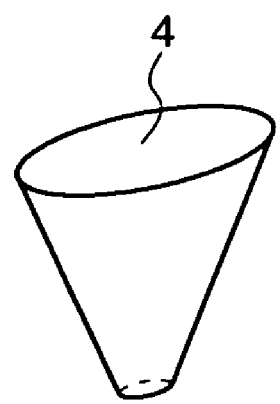

For example, as shown in FIGS. 4A through 4D, the shape of each of the wells 4 is a quadrangular pyramid, a quadrangular truncated pyramid, a circular cone or a circular truncated cone. Furthermore, in this preferred embodiment, the wells 4 having the shape of quadrangular pyramid shown in FIG. 4A are shown as an example.

The reverse 1b of the sample handling plate 1 has lightening portions (recessed portions) 6, each of which has the same shape as that of each of the wells 4 on the side of the surface 1a and the number of which is the same as that of the wells 4. The lightening portions 6 are arranged at the same intervals as those of the wells 4 so as to be displaced by a half pitch from the wells 4. Thus, the total volume of all of the lightening portions 6 on the side of the reverse 1b of the sample handling plate 1 is equal to the total volume of all of the wells 4 on the side of the surface 1a.

As shown in FIG. 2, the sample handling plate 1 having such a shape may be molded by injecting a molten resin into a cavity 2 of a die via an injection molding gate 3, transferring the shape of the cavity 2 of the die, cooling the die and taking a molded article out of the cavity 2.

The sample handling plate 1 thus formed has the reverse 1b which is substantially the same shape as that of the surface 1a, the total volume of all of the lightening portions 6 on the side of the reverse 1b being equal to the total volume of all of the wells 4 on the side of the surface 1a. Therefore, the amount of shrinkage on the side of the surface 1a is equal to that on the side of the reverse 1b after the injection molding, so that it is possible to prevent the plate 1 from warping.

Then, a very small amount of DNA is housed in each of the wells 4 of the sample handling plate 1 thus formed in this preferred embodiment, and specific sites of the DNA are amplified in a short time by the PCR method (the polymerase chain reaction method) to form a microarray (DNA chip) wherein thousands wells 4 housing therein a sufficient amount of DNA fragment (gene fragment) are densely arranged. Thereafter, a specimen (cDNA) treated with a fluorescence dye is injected into each of the wells 4 of the sample handling plate 1, so that the specimen is hybridized with the DNA fragment amplified in each of the wells 4 of the sample handling plate 1. Then, the cDNA in each of the wells 4 of the sample handling plate 1 is irradiated with light beams exciting the fluorescence dye, and fluorescence is detected by a photo detector. Thus, it is possible to identify the specimen hybridized with the DNA fragment, so that it is possible to reveal the function of each of genes.

In the above described sample handling plate 1 in this preferred embodiment, the lightening portions 6 substantially having the same shape as that of the wells 4 formed in the surface 1a are formed in the reverse 1b, and the volume of recessed portions on the side of the surface 1a is substantially equal to the volume of recessed portions on the side of the reverse 1b. Thus, the amounts of shrinkage on the side of the surface 1a and on the side of the reverse 1b with respect to the central plane in thickness directions can be equal to each other after the injection molding, so that it is possible to prevent the plate from warping. As a result, since the warpage of the sample handling plate 1 in this preferred embodiment is suppressed to precisely arrange the wells 4, even if laser light having a narrow focal point is used as illumination light for irradiating each of the wells 4, it is difficult for the focal point of the illumination light to be displaced from the sample to be analyzed, so that it is possible to precisely analyze the sample.

Since the shape of the lightening portions 6 formed in the reverse 1b of the sample handling plate 1 in this preferred embodiment is the same as that of the wells 4 formed in the surface 1a, if the sample handling plate 1 is turned upside down to use the lightening portions 6 as wells, it is possible to ensure wells twice as many as those when the wells 4 are formed only on the side of the surface 1a.

Since the wells 4 formed on the side of the surface 1a of the sample handling plate 1 in this preferred embodiment are displaced by a half pitch from the lightening portions 6 formed on the side of the reverse 1*b*, the bottom of each of the lightening portions 6 can be arranged between adjacent two of the wells 4, so that the plate 1 can be thinner than that when the wells 4 formed on the side of the surface 1*a* face the lightening portions 6 formed on the side of the reverse 1*b*.

Figure 5:
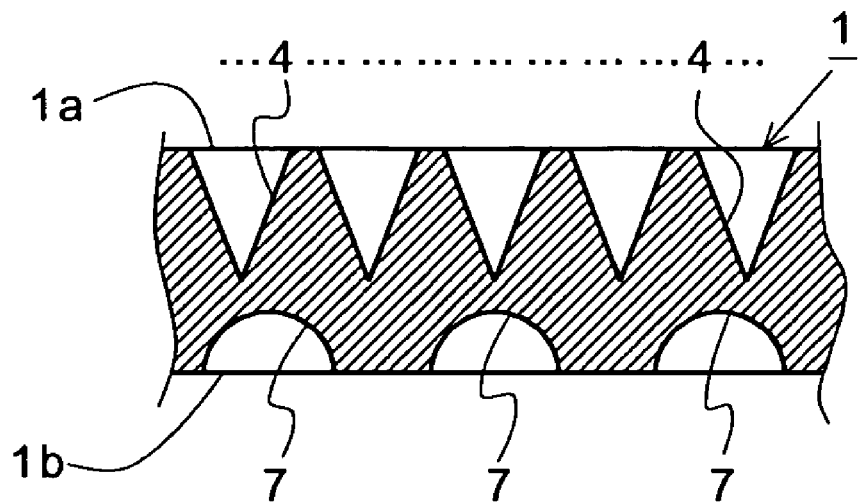
FIG. 5 is an enlarged sectional view showing a part of a first modified example of the preferred embodiment of a sample handling plate according to the present invention.
Figure 6:
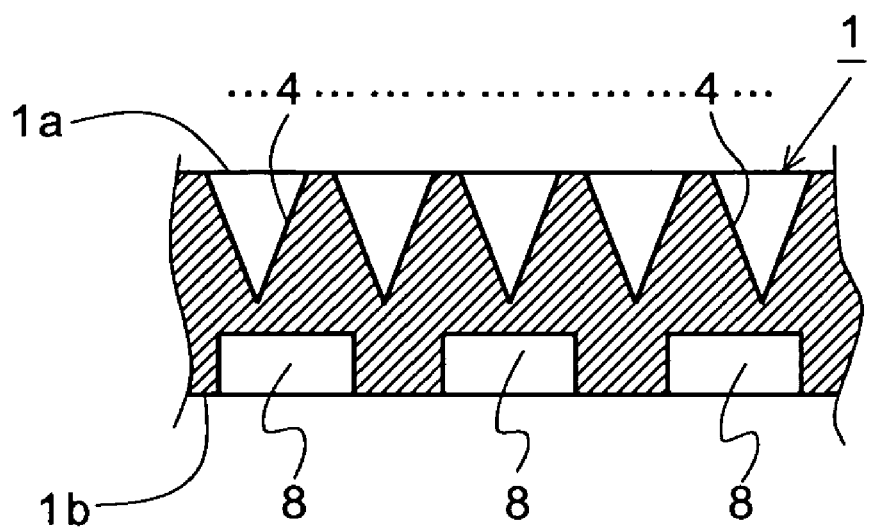
FIG. 6 is an enlarged sectional view showing a part of a second modified example of the preferred embodiment of a sample handling plate according to the present invention.

While the shape of the lightening portions 6 formed in the reverse 1*b* of the sample handling plate 1 in this preferred embodiment has been substantially the same as that of the wells 4, the present invention should not be limited thereto. For example, lightening portions 7 being substantially semispherical recessed portions as shown in FIG. 5, lightening portions 8 being substantially prismatic recessed portions as shown in FIG. 6, or lightening portions being recessed portions having other shapes may be formed. If such lightening portions 7 or 8 shown in FIG. 5 or 6 are formed, the total volume of all of the wells 4 on the side of the surface 1*a* is set to be substantially equal to the total volume of all of the lightening portions 7 or 8 on the side of the reverse 1*b* so that the amount of shrinkage on the side of the surface 1*a* of the sample handling plate 1 is equal to that on the side of the reverse 1*b* thereof after the injection molding.

Figure 7:
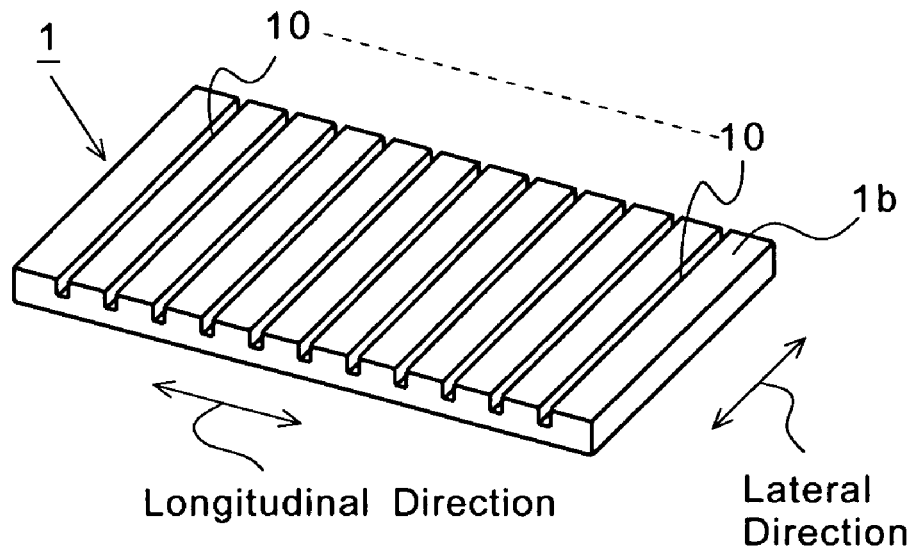
FIG. 7 is a perspective view showing the reverse of a third modified example of the preferred embodiment of a sample handling plate according to the present invention.
Figure 8:
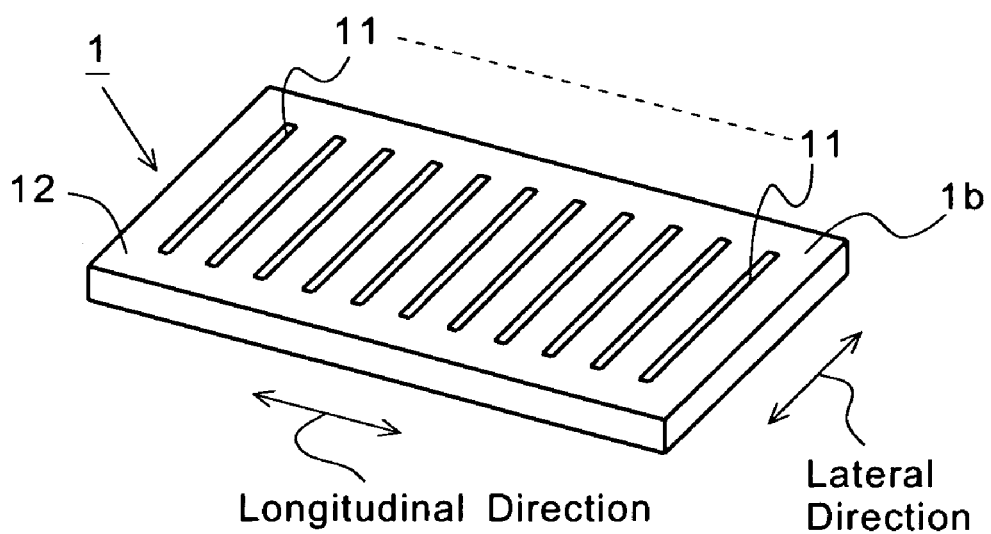
FIG. 8 is a perspective view showing the reverse of a fourth modified example of the preferred embodiment of a sample handling plate according to the present invention.

As shown in FIGS. 7 and 8, a large number of grooves serving as lightening portions 10 and 11 may be formed on the side of the reverse 1*b* of the sample handling plate 1 so as to extend in lateral directions of the sample handling plate 1 in parallel to each other and so as to be spaced from each other at intervals in longitudinal directions. The lightening portions (grooves) 10 shown in FIG. 7 are formed so as to extend over the full width in lateral directions of the sample handling plate 1. On the other hand, the lightening portions (grooves) 11 shown in FIG. 8 are formed in a region substantially corresponding to the well forming region 5 on the side of the surface 1*a* of the sample handling plate 1 (see FIG. 1) so as to be surrounded by a frame region 12 (a region in which the grooves serving as the lightening portions 11 are not formed). Also in such modified examples, the total volume of all of the lightening portions 10, 11 on the side of the reverse 1*b* is substantially equal to the total volume of all of the wells 4 on the side of the surface 1*a*, so that the amount of shrinkage on the side of the surface 1*a* is equal to that on the side of the reverse 1*b* after the injection molding.

Figure 9:
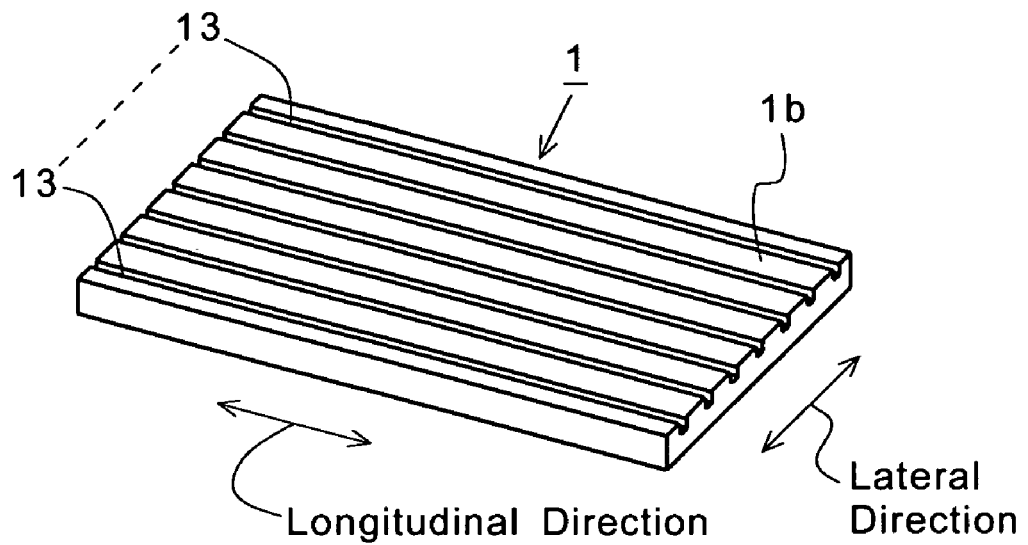
FIG. 9 is a perspective view showing the reverse of a fifth modified example of the preferred embodiment of a sample handling plate according to the present invention.
Figure 10:
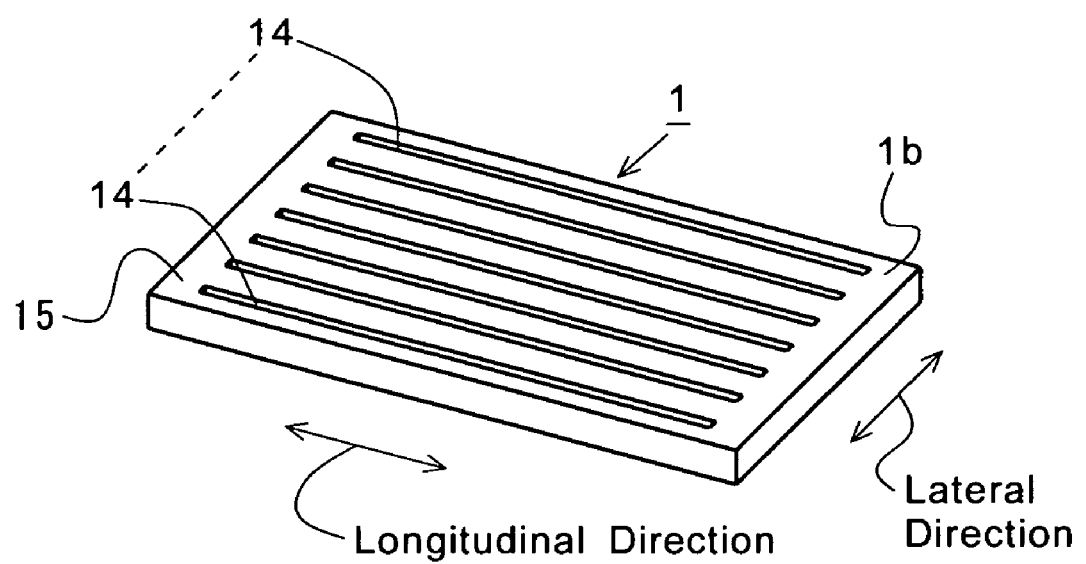
FIG. 10 is a perspective view showing the reverse of a sixth modified example of the preferred embodiment of a sample handling plate according to the present invention.

As shown in FIGS. 9 and 10, a large number of grooves serving as lightening portions 13 and 14 may be formed on the side of the reverse 1*b* of the sample handling plate 1 so as to extend in longitudinal directions of the sample handling plate 1 in parallel to each other and so as to be spaced from each other at intervals in lateral directions of the sample handling plate 1. The lightening portions (grooves) 13 shown in FIG. 9 are formed so as to extend over the full length in longitudinal directions of the sample handling plate 1. On the other hand, the lightening portions (grooves) 14 shown in FIG. 10 are formed in a region substantially corresponding to the well forming region 5 on the side of the surface 1*a* of the sample handling plate 1 (see FIG. 1) so as to be surrounded by a frame region 15 (a region in which the grooves are not formed). Also in such modified examples, the total volume of all of the lightening portions 13, 14 on the side of the reverse 1*b* is substantially equal to the total volume of all of the wells 4 on the side of the surface 1*a*, so that the amount of shrinkage on the side of the surface 1*a* is equal to that on the side of the reverse 1*b* after the injection molding.

Figure 11:
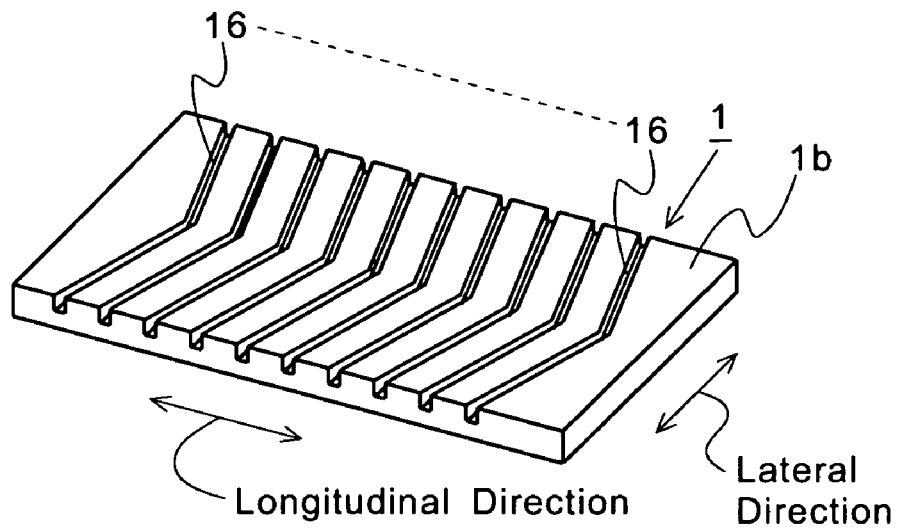
FIG. 11 is a perspective view showing the reverse of a seventh modified example of the preferred embodiment of a sample handling plate according to the present invention.

As shown in FIG. 11, a large number of grooves serving as lightening portions 16 may be formed on the side of the reverse 1*b* of the sample handling plate 1 so as to extend in a substantially V-shape and so as to be spaced from each other at intervals in longitudinal directions. In this case, the lightening portions 16 shown in FIG. 11 may be formed in a region substantially corresponding to the well forming region 5 on the side of the surface 1*a* of the sample handling plate 1 (see FIG. 1) so as to be surrounded by a frame region (a region in which the grooves are not formed).

Figure 12:
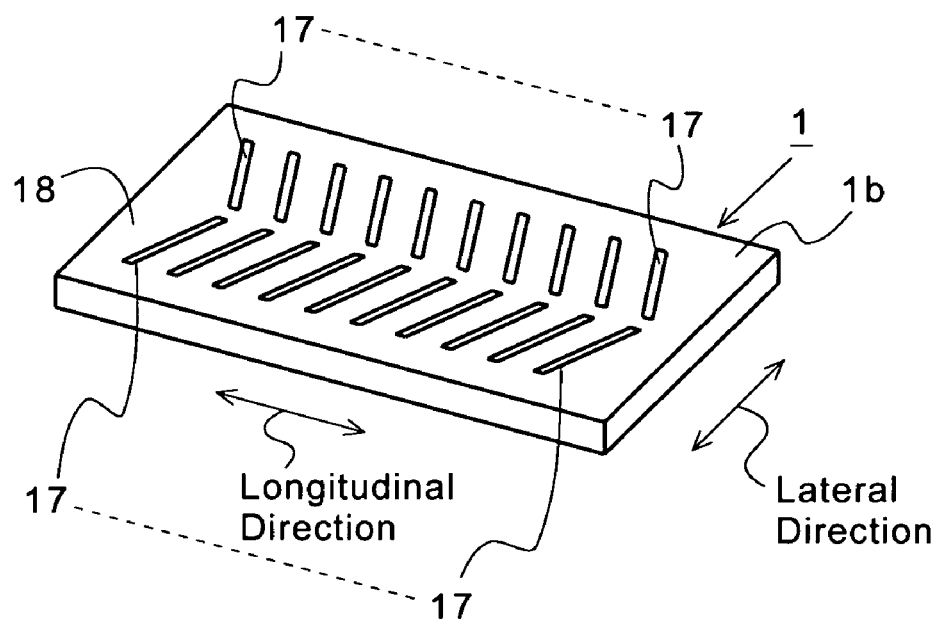
FIG. 12 is a perspective view showing the reverse of an eighth modified example of the preferred embodiment of a sample handling plate according to the present invention.

As shown in FIG. 12, a large number of grooves serving as lightening portions 17 may be formed on the side of the reverse 1*b* of the sample handling plate 1 in a region, which substantially corresponds to the well forming region 5 on the side of the surface 1*a* of the sample handling plate 1 (see FIG. 1), except for a longitudinally extending central portion along a longitudinal center line on the side of the surface 1*b* of the sample handling plate 1. The lightening portions 17 extend in directions oblique from the longitudinal center line on the side of the surface 1*b* of the sample handling plate 1 so as to be symmetrical with respect to the longitudinal center line, and are arranged so as to be spaced from each other at intervals in longitudinal directions. In this case, the lightening portions 17 may be formed so as to be surrounded by a frame region (a region in which the grooves are not formed). Also in such modified examples, the total volume of all of the lightening portions 17 on the side of the reverse 1*b* is substantially equal to the total volume of all of the wells 4 on the side of the surface 1*a*, so that the amount of shrinkage on the side of the surface 1*a* is equal to that on the side of the reverse 1*b* after the injection molding.

Figure 13:
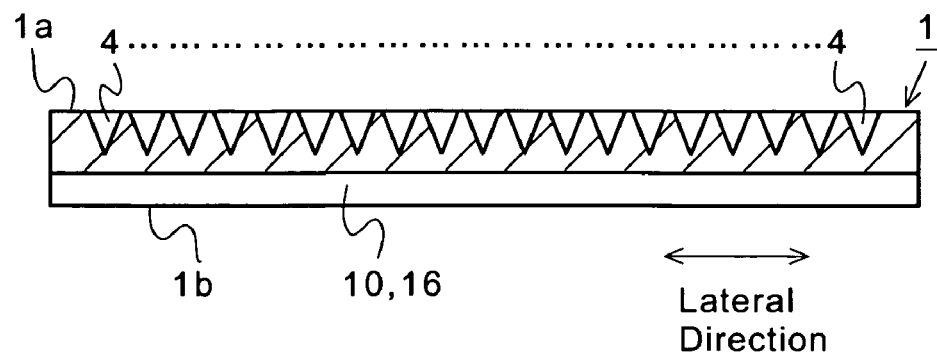
FIG. 13 is a sectional view of the preferred embodiment of a sample handling plate according to the present invention, which is taken along a groove serving as a lightening portion.
Figure 14:
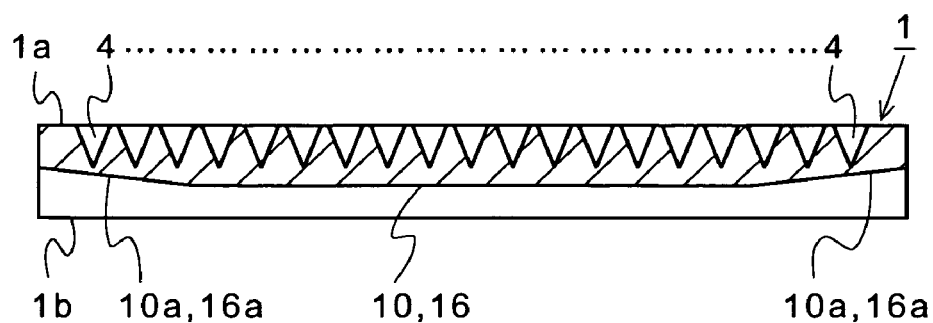
FIG. 14 is a sectional view showing a ninth modified example of the preferred embodiment of a sample handling plate according to the present invention, which corresponds to FIG. 13.

The lightening portions 10 and 16 formed on the side of the reverse 1*b* of the sample handling plate 1 as shown in FIGS. 7 and 11 substantially have the same depth as shown in FIG. 13, respectively. However, as shown in FIG. 14, inclined groove portions 10*a* and 16*b*, the depth of which gradually increases as a distance from each of both ends in lateral directions decreases, may be formed on both end portions in lateral directions, respectively. If the sample handling plate 1 is thus formed, the velocity of a molten resin, which is injected from the injection molding gate 3 to flow in a portion of the cavity 2 corresponding to the well forming region 5, is equal to the velocity of the molten resin which is injected from the injection molding gate 3 to flow in a portion of the cavity 2 corresponding to the frame region 20 on both sides of the well forming region 5 in lateral directions. That is, if the sample handling plate 1 is not formed as described above, the flow resistance of the molten resin in the well forming region 5, in which the large number of wells 4 are formed, is greater than that in the frame region 20 on both sides of the well forming region 5 in lateral directions (see FIG. 1). Therefore, the molten resin flowing in the frame region 20 on both sides of the well forming region 5 in lateral directions flows prior to the molten resin flowing in the well forming region 5, so that there are some cases where a weld line (a thin line as a hair line appears when the molten resins meet each other) may be produced in the junction portion of the molten resins. However, if the cross section of the frame region 20 on both sides of the well forming region 5 in lateral directions is narrowed (decreased) so that it is difficult to flow the molten resin, the flow velocity of the molten resin flowing in the well forming region 5 can be equal to that in the frame region 20 on both sides of the well forming region 5 in lateral directions. As a result, according to the sample handling plate 1 in this modified example, it is possible to prevent weld lines from being produced by the uneven flow velocity of the resin on the side of the edge 21 farthest from the injection molding gate 3 (see FIG. 1), and it is possible to prevent the shape of the die from being defectively transferred by the production of weld lines, so that it is possible to precisely form the sample handling plate 1 including the wells 4.

Figure 15A:
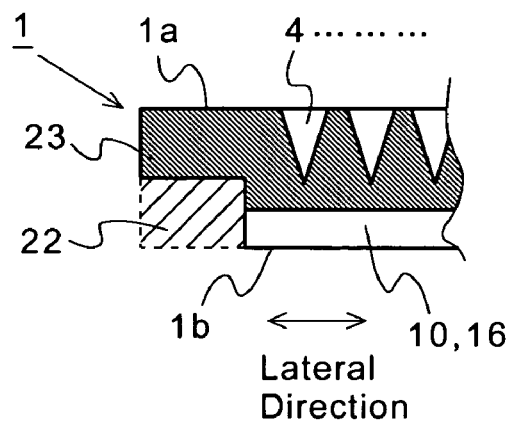
FIGS. 15A and 15B are enlarged sectional views showing a part of a tenth modified example of the preferred embodiment of a sample handling plate according to the present invention, which is taken in lateral directions of the sample handling plate.
Figure 15B:
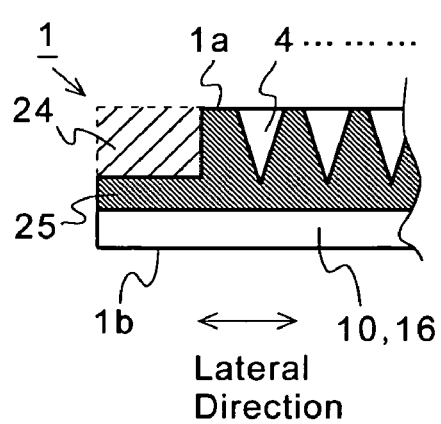

As shown in FIGS. 15A and 15B, in order to prevent weld lines from being produced and in order to prevent the shape of the die from being defectively transferred by the weld lines, the thickness of the frame portion 20 on both sides of the well forming region 5 in lateral directions may be continuously or intermittently decreased in longitudinal directions to throttle the flow of the molten resin to uniform the flow velocity of the molten resin in the well forming region 5 and in the frame region 20 on both sides of the well forming region 5 in lateral directions. Furthermore, FIG. 15A shows a state that thin portions 23 are formed by cutting slanting line portions 22 out on the side of the reverse 1b of the sample handling plate 1, and FIG. 15B shows a state that thin portions 25 are formed by cutting slanting line portions 24 out on the side of the surface 1a of the sample handling plate 1.

While the sample handling plate 1 has been precisely formed by the injection molding in the above described preferred embodiment, the present invention should not be limited thereto. For example, the present invention may be applied to the compression molding method for heating and pressurizing resin powder, which is filled in a die, to transfer the shape of the die, or a molding method for irradiating an ultraviolet curable resin, which is applied on a die, with ultraviolet to cure the resin to transfer the shape of the die.

While the construction for preventing the sample handling plate 1 from warping has been described in the above described preferred embodiment, the present invention should not be limited thereto. As will be described later, reinforcing ribs may be formed on the side of the reverse 1b of the sample handling plate 1. Alternatively, a metal body or a member of a material, such as a ceramic, having a lower shrinkage percentage (a lower coefficient of linear expansion) than that of the plastic of the sample handling plate 1, may be formed on the side of the reverse 1b of the sample handling plate 1 so as to be integrated therewith.

While the plastic plate has been described in detail in the above described preferred embodiment, the present invention should not be limited thereto, but a plate of a material, such as a glass, other than plastics may have the same construction as that in the above described preferred embodiment to effectively prevent the plate from warping.

EXAMPLE 1

Figure 16:
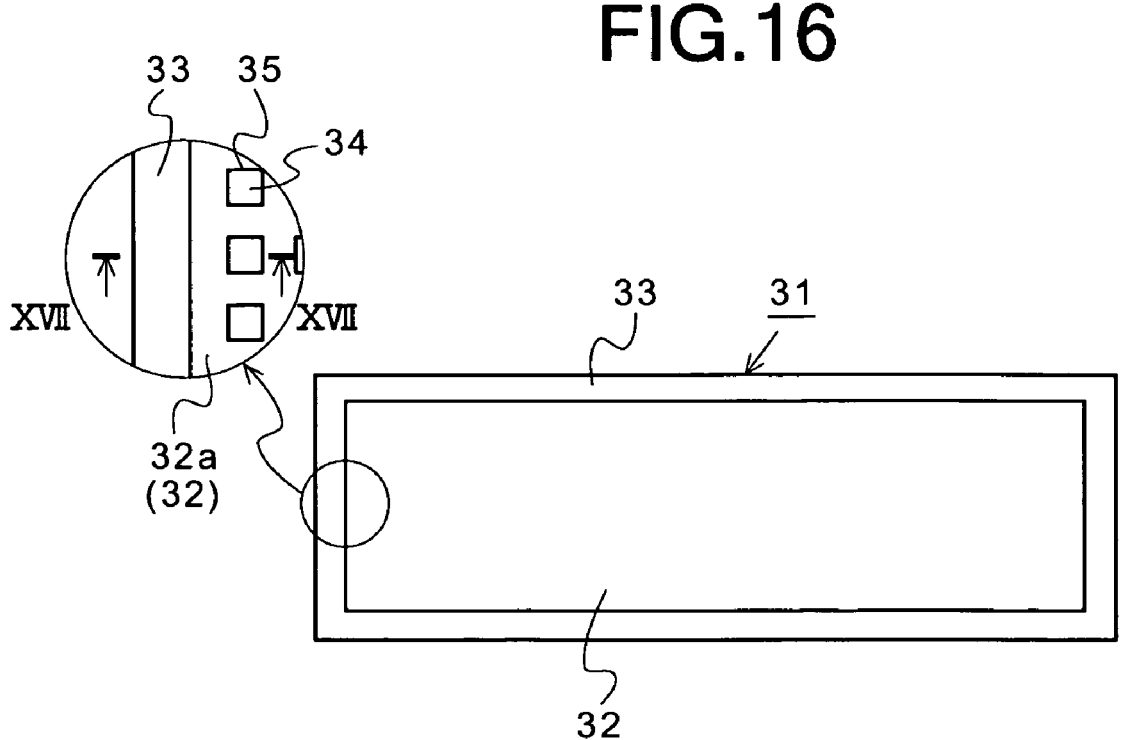
FIG. 16 is a plan view of a first example of a sample handling plate according to the present invention.
Figure 17:
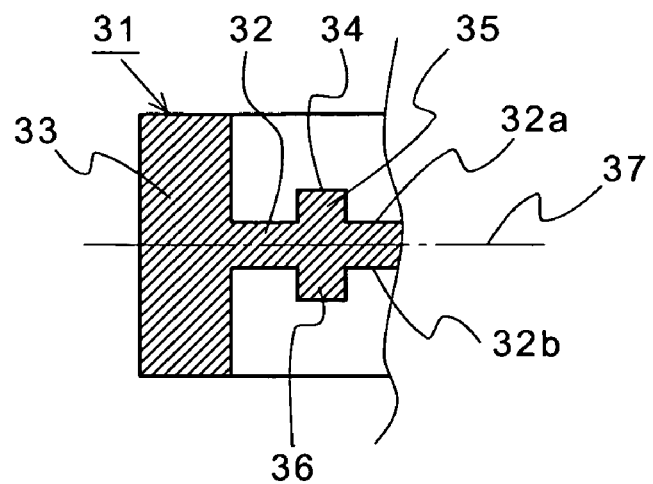
FIG. 17 is a sectional view taken along line XVII-XVII of FIG. 16.

FIGS. 16 and 17 show a sample handling plate 31 in Example 1 according to the present invention. As shown in these figures, the sample handling plate 31 in this example comprises a thin plate portion 32, and a frame portion 33 surrounding the periphery of the plate portion 32. The plate portion 32 is connected to the frame portion 33 so as to be arranged in a substantially central portion of the frame portion 33 in thickness directions. The surface 32a of the plate portion 32 has a large number of minute protrusions 35, each of which has a top face 34 to which a sample (DNA fragment or the like) to be analyzed is allowed to adhere. The reverse 32b of the plate portion 32 has a large number of minute protrusions 36 which have the same shape as that of the protrusions 35 on the side of the surface 32a of the plate portion 32 and which are arranged so as to correspond to the protrusions 35. Thus, the shape of the sample handling plate 31 is symmetrical with respect to the central plane 37 in thickness directions. As a result, the amount of shrinkage on the side of the surface 32a of the plate portion 32 is equal to that on the side of the reverse 32b of the plate portion 32 during cooling after the injection molding, so that it is possible to suppress the warpage of the plate portion 32. Furthermore, in this example, the thickness of the plate portion 32 is set to be about 0.8 mm, and the height of the protrusions 35 is set to be in the range of from 100 μm to 200 μm. The diameter or length of a side of the top face 34 of each of the protrusions 35 is set to be substantially equal to the diameter or length of a side of the opening portion of each of the wells 4 in the above described preferred embodiment, and the pitch between adjacent two of the protrusions 35 is also set to be substantially equal to the pitch between adjacent two of the wells 4 in the above described preferred embodiment.

EXAMPLE 2

Figure 18:
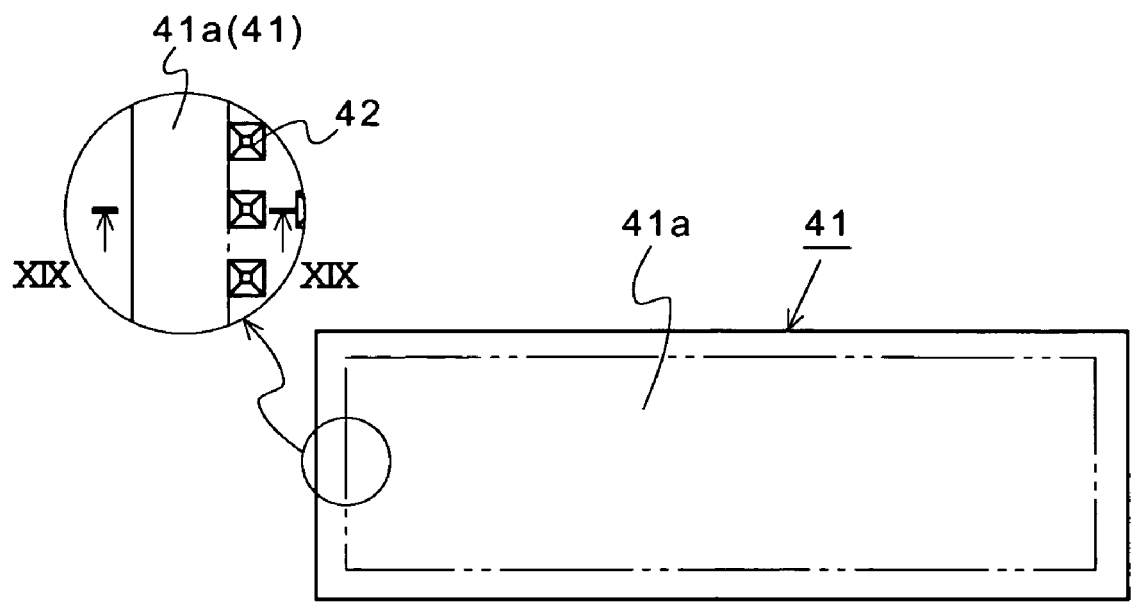
FIG. 18 is a plan view of a second example of a sample handling plate according to the present invention.
Figure 19:
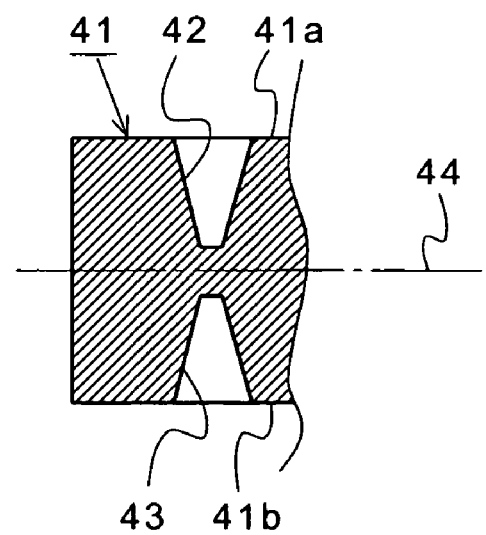
FIG. 19 is a sectional view taken along line XIX-XIX of FIG. 18.

FIGS. 18 and 19 show a sample handling plate 41 in Example 2 according to the present invention. As shown in these figures, the sample handling plate 41 in this example has minute wells (recessed portions) 42 on the side of the surface 41a thereof, and recessed portions (lightening portions) 43 on the side of the reverse 41b thereof. The recessed portions 43 have the same shape as that of the wells 42. The wells 42 and the recessed portions 43 are symmetrical with respect to a central plane 44 in thickness directions of the sample handling plate 41. Thus, the amount of shrinkage on the side of the surface 41a is equal to that on the side of the reverse 41b during cooling after the injection molding, so that it is possible to suppress the warpage of the sample handling plate 41.

EXAMPLE 3

Figure 20:
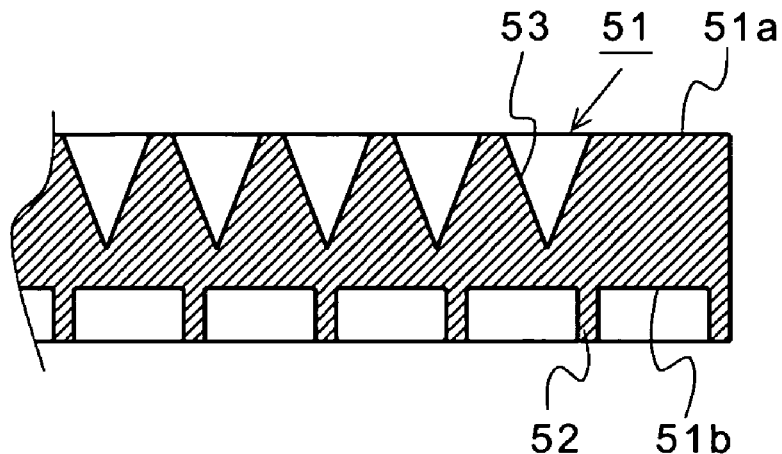
FIG. 20 is an enlarged sectional view showing a part of a third example of a sample handling plate according to the present invention.
Figure 21:
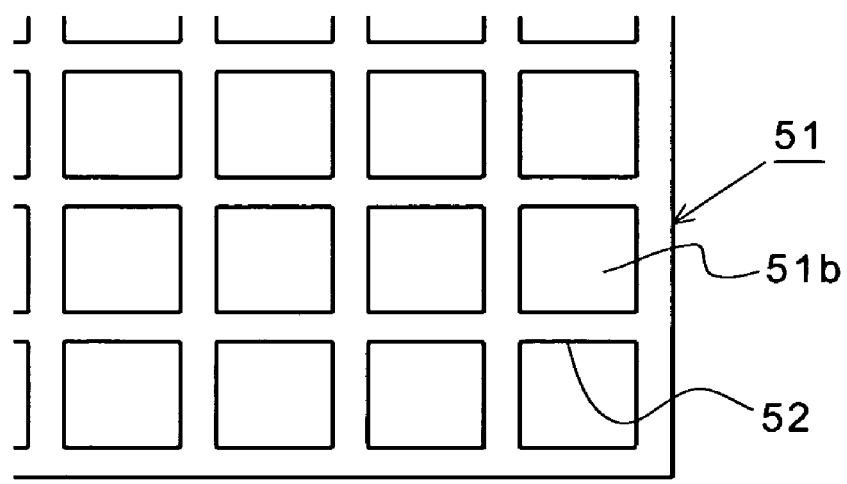
FIG. 21 is a bottom view of the part of the sample handling plate of FIG. 20.

FIGS. 20 and 21 show a sample handling plate 51 in Example 3 according to the present invention. As shown in these figures, the sample handling plate 51 in this example has a lattice-shaped reinforcing rib 52 on the side of the reverse 51b thereof. When the sample handling plate 51 is used in a heating environment for causing a temperature difference between the surface and reverse thereof, the reinforcing rib 52 prevents the warpage of the sample handling plate 51 due to the temperature difference between the surface and reverse thereof. Thus, since the warpage of the sample handling plate 51 is prevented even if the sample handling plate 51 in this example is used in a heating environment for causing a temperature difference between the surface and reverse thereof, it is possible to precisely focus irradiation light beams on a sample in each of a large number of minute wells (recessed portions) 53 formed on the side of the surface 51a of the sample handling plate 51, so that it is possible to precisely analyze the sample.

While the large number of wells 53 have been formed on the side of the surface 51a in this example, the present invention should not be limited thereto. For example, the present invention may be applied to a sample handling plate wherein a fine groove (a recessed portion) forming a flow passage, in which a fluid is moved by a driving force, such as electrophoresis, capillarity or differential pressure, is formed on the side of the surface 51a, or to a sample handling plate having a flat surface (having no well or protrusion) to which a large number of samples are allowed to adhere at scattered points.

In this example, the reinforcing rib 52 is preferably formed so as to correspond to at least a region in which the wells 53 are formed. However, the reinforcing rib 52 may be formed so as to correspond to a narrower region than the region in which the wells 53 are formed, as long as the warpage of the sample handling plate 51 can be suppressed in a desired range.

While the lattice-shaped reinforcing rib 52 has been formed in this example, the present invention should not be limited thereto, but the reinforcing rib 52 has a shape corresponding to the warpage.

EXAMPLE 4

Figure 22:
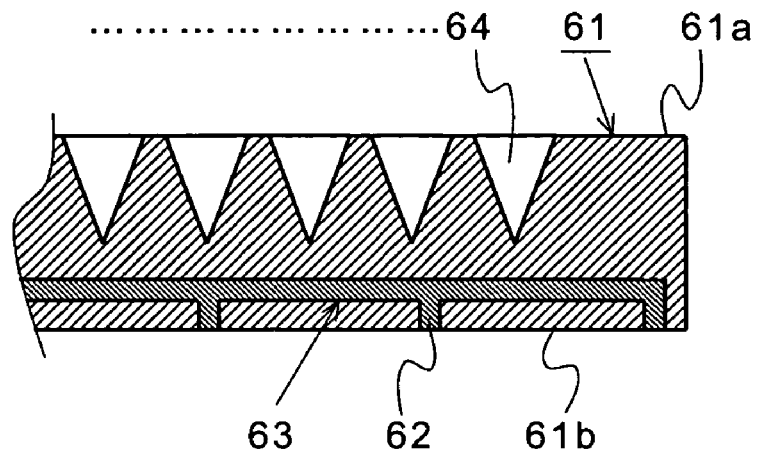
FIG. 22 is an enlarged sectional view showing a part of a fourth example of a sample handling plate according to the present invention.
Figure 23:
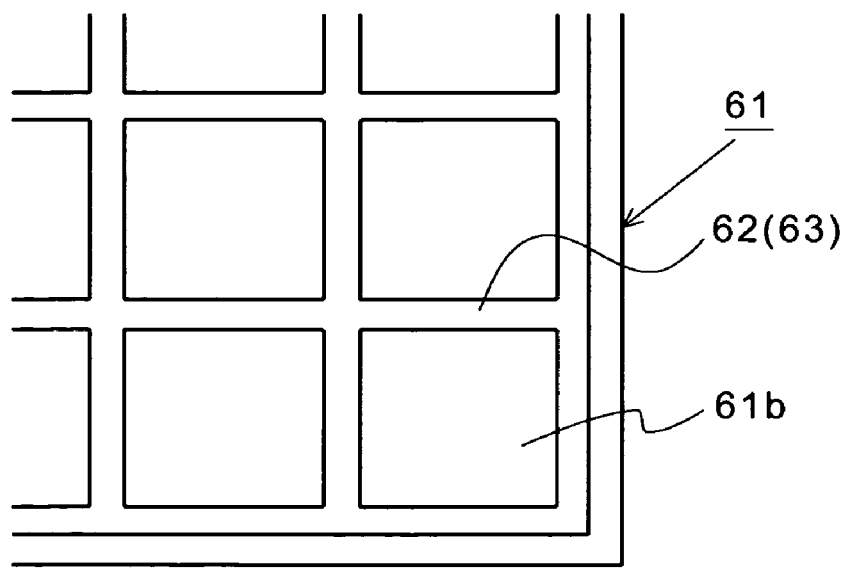
FIG. 23 is a bottom view of the part of the sample handling plate of FIG. 22.
Figure 24:
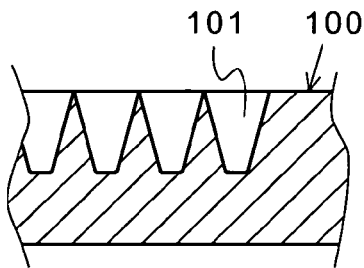
FIG. 24 is an enlarged sectional view of a part of a plate serving as a first conventional example.
Figure 25:
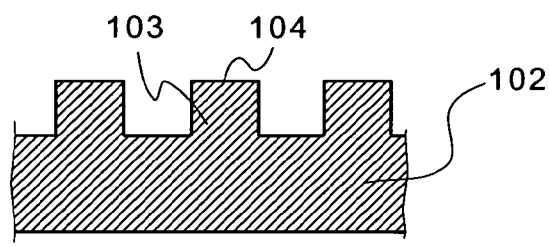
FIG. 25 is an enlarged view of a part of a plate serving as second and third conventional examples.
Figure 26:
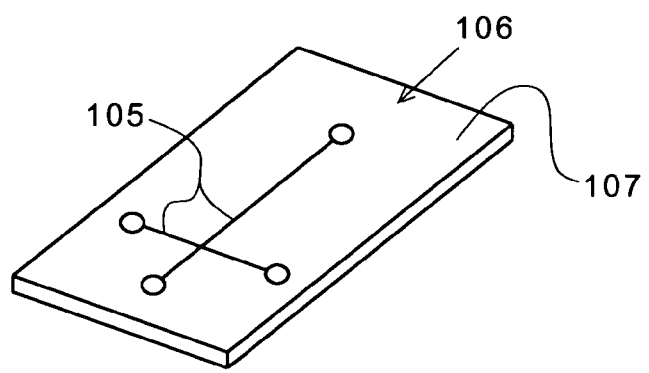
FIG. 26 is a perspective view of a plate serving as a fourth conventional example.
Figure 27:
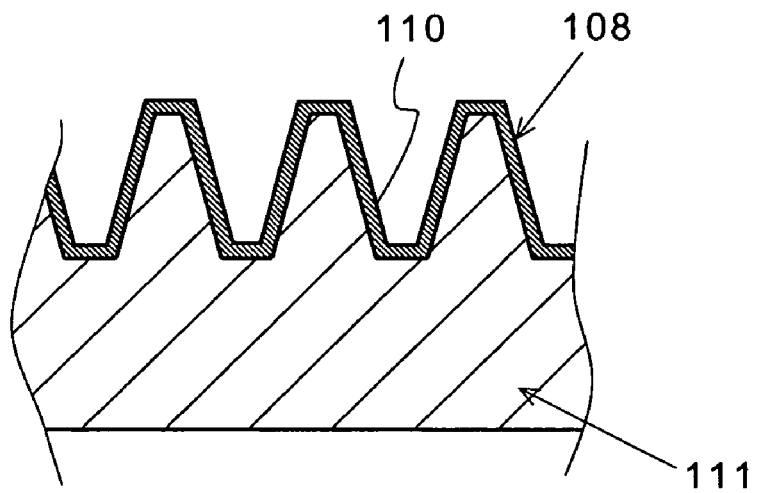
FIG. 27 is an enlarged sectional view of a part of a plate serving as a sixth conventional example.
Figure 28:
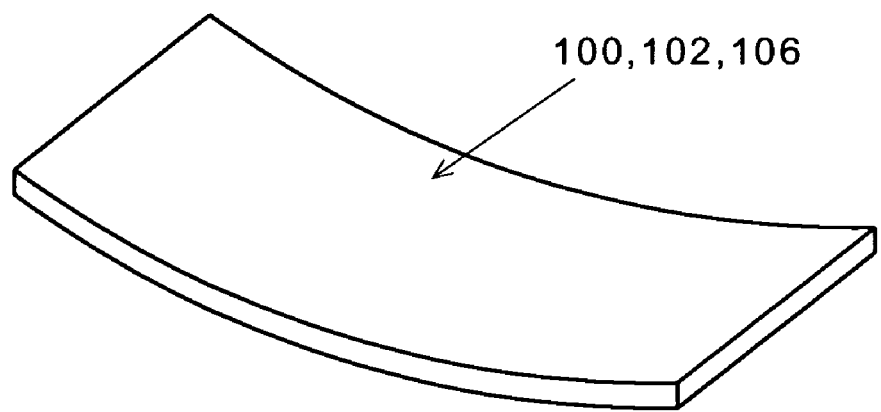
FIG. 28 is a perspective view showing a state that a conventional plate warps.

FIGS. 22 and 23 show a sample handling plate 61 in Example 4 according to the present invention. As shown in these figures, the sample handling plate 61 in this example has a sheet-like metal body 63 which has a lattice-shaped rib 62 on the side of the reverse 61b thereof and which is embedded therein. The metal body 63 has a smaller amount of thermal expansion (a lower coefficient of thermal expansion) than that of the resin material of the sample handling plate 61, and has a higher rigidity than that of the resin material of the sample handling plate 61. Therefore, if the sample handling plate 61 is used in a heating environment, it is possible to suppress the deformation of the sample handing plate 61, and it is possible to focus irradiation light beams on a sample in each of a large number of minute wells (recessed portions) 64 on the side of the surface 61a of the sample handling plate 61, so that it is possible to precisely analyze the sample.

While the large number of wells 64 have been formed on the side of the surface 61a in this example, the present invention should not be limited thereto. For example, the present invention may be applied to a sample handling plate wherein a fine groove (a recessed portion) forming a flow passage, in which a fluid is moved by a driving force, such as electrophoresis, capillary or differential pressure, is formed on the side of the surface 61a, or to a sample handling plate having a flat surface (having no well or protrusion) to which a large number of samples are allowed to adhere at scattered points.

In this example, the metal body 63 is preferably arranged so as to correspond to at least a region in which the wells 64 are formed. However, the metal body 63 may be formed so as to correspond to a narrower region than the region in which the wells 64 are formed, as long as the warpage of the sample handling plate 61 can be suppressed in a desired range.

The sample handling plate according to the present invention can be used for analyzing very small amounts of various samples (e.g., micro vital substances such as viruses and bacteria, vital formations such as cells and biopolymers, organic compounds other than biopolymers, inorganic substances and inorganic compounds). For example, if the genome information of various biological species is simultaneously analyzed by a single sample handling plate, it is possible to increase the analyzing speed for the genome information. In addition, the sample handling plate according to the present invention can more surely prevent adjacent samples from being mixed with each other than a case where very small amounts of samples are caused to adhere to a flat plate by means of a spotting device, so that it is possible to precisely analyze a very small amount of sample in each of the wells. In addition, the sample handling plate according to the present invention is designed to hold a very small amount of sample injected into each of the wells, so that the sample handling plate can also be used as a reactor in the PCR method for amplifying DNAs. Moreover, the sample handling plate according to the present invention can be used as a chip for a microfluidic device which is designed to utilize electrophoresis, capillary or differential pressure as a driving force to move a fluid in a fine flow passage to carry out synthesis, separation, analysis or the like, so that the sample handling plate can be effectively used for separating and analyzing a very small amount of substance.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A sample handling plate comprising:
   a rectangular plate member having a surface and a reverse, said plate member having a thickness of from about 1.0 mm to about 1.5 mm;
   thousands of fine recessed portions formed in said surface of the plate member, said fine recessed portions being arranged at regular intervals of from about 0.3 mm to about 1.0 mm, each of said fine recessed portions having a volume of tens nanoliters; and
   a recessed portion formed in said reverse of the plate member, said recessed portion having a volume which is equal to a total volume of all of said fine recessed portions.

2. A sample handling plate comprising:
   a rectangular plate member having a surface and a reverse, said plate member having a thickness of from about 1.0 mm to about 1.5 mm;
   thousands of first fine recessed portions formed in said surface of the plate member, said first fine recessed portions being arranged at regular intervals of from about 0.3 mm to about 1.0 mm, each of said first fine recessed portions having a volume of tens nanoliters; and
   a plurality of second fine recessed portions formed in said reverse of the plate member, said second fine recessed portions having a total volume which is equal to a total volume of all of said first fine recessed portions.

3. A sample handling plate as set forth in claim 2, wherein each of said second fine recessed portions has the same shape as that of each of said first fine recessed portions.

4. A sample handling plate as set forth in claim 3, wherein said second fine recessed portions are arranged at the same intervals as those of said first fine recessed portions so as to be displaced from said first fine recessed portion by half of each of said intervals.

5. A sample handling plate as set forth in claim 1, wherein each of said fine recessed portions has a circular or square opening, the diameter of said circular opening or the length of one side of said square opening is in the range of from about 0.2 mm to about 1.0 mm.

6. A sample handling plate as set forth in claim 2, wherein each of said first fine recessed portions has a circular or square opening, the diameter of said circular opening or the length of one side of said square opening is in the range of from about 0.2 mm to about 1.0 mm.

7. A sample handling plate as set forth in claim 1, wherein said fine recessed portions are arranged at regular intervals of from about 0.3 mm to 0.5 mm.

8. A sample handling plate as set forth in claim 2, wherein said first fine recessed portions are arranged at regular intervals of from about 0.3 mm to about 0.5 mm.

9. A sample handling plate as set forth in claim 1, wherein each of said fine recessed portions has a circular or square opening, the diameter of said circular opening or the length of one side of said square opening is in the range of from about 0.2 mm to about 0.5 mm.

10. A sample handling plate as set forth in claim 2, wherein each of said first fine recessed portions has a circular or square opening, the diameter of said circular opening or the length of one side of said square opening is in the range of from about 0.2 mm to about 0.5 mm.

11. A sample handling plate comprising:
a plate body having a surface and a reverse;
thousands of fine recessed portions formed in said surface of the plate body, each of said fine recessed portions having a volume of tens nanoliters; and
a recessed portion formed in said reverse of the plate body, said recessed portion being formed so as to have a volume which is equal to a total volume of all of said fine recessed portions.

12. A sample handling plate comprising:
a plate body having a surface and a reverse;
thousands of first fine recessed portions formed in said surface of the plate body, each of said first fine recessed portions having a volume of tens nanoliters; and
a plurality of second fine recessed portions formed in said reverse of the plate body, said second fine recessed portions being formed so as to have a total volume which is equal to a total volume of all of said first fine recessed portions.

13. A sample handling plate as set forth in claim 12, wherein each of said second fine recessed portions has the same shape as that of each of said first fine recessed portions.

14. A sample handling plate as set forth in claim 13, wherein said first fine recessed portions are arranged at regular intervals, and said second fine recessed portions are arranged at the same intervals as those of said first fine recessed portions so as to be displaced from said first fine recessed portion by half of each of said intervals.

15. A sample handling plate comprising:
a plate body having a surface and a reverse;
a plurality of fine recessed portions formed in said surface of the plate body; and
a recessed portion formed in said reverse of the plate body, said recessed portion being formed so as to have a volume which is equal to a total volume of all of said fine recessed portions.

16. A sample handling plate comprising:
a plate body having a surface and a reverse;
a plurality of first fine recessed portions formed in said surface of the plate body; and
a plurality of second fine recessed portions formed in said reverse of the plate body, said second fine recessed portions being formed so as to have a total volume which is equal to a total volume of all of said first fine recessed portions.

17. A sample handling plate as set forth in claim 16, wherein each of said second fine recessed portions has the same shape as that of each of said first fine recessed portions.

18. A sample handling plate as set forth in claim 17, wherein said first fine recessed portions are arranged at regular intervals, and said second fine recessed portions are arranged at the same intervals as those of said first fine recessed portions so as to be displaced from said first fine recessed portion by half of each of said intervals.

* * * * *